US012514623B2

(12) United States Patent
Touchet et al.

(10) Patent No.: US 12,514,623 B2
(45) Date of Patent: Jan. 6, 2026

(54) ORTHOPEDIC PLATE FOR TREATMENT OF TIBIAL FRACTURES AND RELATED METHODS

(71) Applicant: Trilliant Surgical LLC, Houston, TX (US)

(72) Inventors: Tyler Joseph Touchet, Cypress, TX (US); Mia Fiacchi, Houston, TX (US)

(73) Assignee: Trilliant Surgical LLC, Houston, TX (US)

(*) Notice: Subject to any disclaimer, the term of this patent is extended or adjusted under 35 U.S.C. 154(b) by 197 days.

(21) Appl. No.: 18/082,072

(22) Filed: Dec. 15, 2022

(65) Prior Publication Data

US 2023/0190344 A1 Jun. 22, 2023

Related U.S. Application Data

(60) Provisional application No. 63/290,836, filed on Dec. 17, 2021.

(51) Int. Cl.
*A61B 17/80* (2006.01)
*A61B 17/00* (2006.01)
(Continued)

(52) U.S. Cl.
CPC ...... *A61B 17/8004* (2013.01); *A61B 17/8061* (2013.01); *A61B 2017/00526* (2013.01); *A61B 2017/564* (2013.01); *A61B 2017/681* (2013.01)

(58) Field of Classification Search
CPC ............ A61B 17/8061; A61B 17/8085; A61B 17/8004
See application file for complete search history.

(56) References Cited

U.S. PATENT DOCUMENTS 7,942,877 B2 5/2011 Medoff
8,100,954 B2 1/2012 Kay et al.
(Continued)

FOREIGN PATENT DOCUMENTS

EP 1922003 A2 5/2008
EP 3285671 A1 2/2018
(Continued)

OTHER PUBLICATIONS

International Search Report and Written Opinion, mailed Apr. 17, 2023 in PCT/US2022/052996.
(Continued)

*Primary Examiner* — Olivia C Chang
(74) *Attorney, Agent, or Firm* — Veros Legal Solutions, LLP

(57) ABSTRACT

An orthopedic tension band plate includes proximal and distal portions. The proximal portion includes a first proximal aperture configured to receive a first securing member, and a second proximal aperture disposed distal of the first proximal aperture and configured to receive a second securing member. The distal portion includes first and second tines extending distally to first and second distal ends having first and second distal apertures configured to receive third and fourth securing members. At least the first and second tines are configured to wrap around and conform to portions of the bone proximate to the fracture and, thereby, convert tensile forces at the fracture into compressive forces when the first through fourth securing members are secured through their respective apertures and into the bone.

32 Claims, 8 Drawing Sheets

(51) Int. Cl.
*A61B 17/56* (2006.01)
*A61B 17/68* (2006.01)

(56) References Cited

U.S. PATENT DOCUMENTS

| | | | |
|---|---|---|---|
| 8,118,848 | B2 | 2/2012 | Ducharme et al. |
| 8,177,818 | B2 | 5/2012 | Wotton, III |
| 8,177,822 | B2 | 5/2012 | Medoff |
| 8,257,405 | B2 | 9/2012 | Haidukewych et al. |
| 8,262,707 | B2 | 9/2012 | Huebner et al. |
| 8,317,842 | B2 | 11/2012 | Graham et al. |
| 8,382,807 | B2 | 2/2013 | Austin et al. |
| 8,475,504 | B2 | 7/2013 | Gillard et al. |
| 8,715,324 | B2 | 5/2014 | Wotton, III |
| 8,808,334 | B2 | 8/2014 | Strnad et al. |
| 8,888,824 | B2 | 11/2014 | Austin et al. |
| 8,906,070 | B2 | 12/2014 | Medoff |
| 9,149,313 | B2 | 10/2015 | Strnad et al. |
| 9,301,789 | B2 | 4/2016 | Schonhardt et al. |
| 9,636,157 | B2 | 5/2017 | Medoff |
| 9,795,424 | B2 | 10/2017 | Austin et al. |
| 9,861,407 | B2 | 1/2018 | Early et al. |
| 9,895,180 | B2 | 2/2018 | Early et al. |
| 9,918,761 | B2 | 3/2018 | Early et al. |
| 10,092,337 | B2 | 10/2018 | Austin et al. |
| 10,182,854 | B2 | 1/2019 | Early et al. |
| 10,226,289 | B2 | 3/2019 | Wainscott |
| 10,258,396 | B2 | 4/2019 | Kazanovicz et al. |
| 10,292,741 | B2 | 5/2019 | Austin et al. |
| 10,372,822 | B2 | 8/2019 | Devarakonda et al. |
| 10,413,341 | B2 | 9/2019 | Chaudot et al. |
| 10,507,050 | B2 | 12/2019 | Chatain et al. |
| 10,736,680 | B2 | 8/2020 | Austin et al. |
| 10,918,427 | B2 | 2/2021 | Wainscott |
| 2009/0069851 | A1 | 3/2009 | Gillard et al. |
| 2009/0306724 | A1 | 12/2009 | Leither et al. |
| 2014/0039561 | A1 | 2/2014 | Weiner et al. |
| 2014/0058510 | A1 | 2/2014 | Appenzeller et al. |
| 2014/0107711 | A1* | 4/2014 | Norris ................ A61F 2/30739 606/291 |
| 2016/0278828 | A1 | 9/2016 | Ragghianti |
| 2019/0175237 | A1 | 6/2019 | Treace et al. |
| 2020/0100820 | A1* | 4/2020 | Hollis ................ A61B 17/8863 |
| 2020/0297502 | A1 | 9/2020 | Armacost et al. |
| 2020/0323570 | A1 | 10/2020 | Austin et al. |

FOREIGN PATENT DOCUMENTS

| | | | |
|---|---|---|---|
| EP | 3398526 | A1 | 11/2018 |
| EP | 3398545 | A1 | 11/2018 |
| EP | 3542739 | A1 | 9/2019 |
| WO | 2020062709 | A1 | 4/2020 |
| WO | 2020243181 | A1 | 12/2020 |
| WO | 2023114389 | A1 | 6/2023 |

OTHER PUBLICATIONS

International Preliminary Report on Patentability mailed on Jun. 27, 2024 in WO PCT/US2022/052996.
Medartis, "Olecranon System 2.8," https://medartis.com/en/solutions/upper-extremities/aptus-elbow/olecranon-system-28; accessed: Jul. 15, 2025.
TriMed Inc, "Medial Malleolar Sled," https://trimedortho.com/portfolio-items/medial-malleolar-sled/, accessed: Jul. 11, 2025.
Wegner et al., "Sled fixation for horizontal medial malleolus fractures. Clinical Biomechanics," 42, 92-96. doi: 10.1016/j.clinbiomech.2017 .01.011 (2017).

* cited by examiner

ORTHOPEDIC PLATE FOR TREATMENT OF TIBIAL FRACTURES AND RELATED METHODS

CROSS-REFERENCE TO RELATED APPLICATIONS

This application is related to, and claims priority to U.S. Provisional Patent Application Ser. No. 63/290,836, filed on Dec. 17, 2021, and entitled ORTHOPEDIC PLATE FOR TREATMENT OF TIBIAL FRACTURES AND RELATED METHODS, the contents of which is hereby incorporated by reference in its entirety.

FIELD

The present disclosure relates to implants and/or systems for treatment of bone fractures and related methods.

BACKGROUND

Different types of loads cause different types of bone fracture patterns. For example, axial loads can cause an avulsion fracture pattern, where a piece of the bone attached to a ligament or tendon is pulled away. This fracture pattern has both compressive and tensile forces acting upon the fracture. In this instance, the tensile forces are present but compressive forces between the bone fragments are no longer sufficient, causing gaps. To close these gaps between bone fragments, the tensile forces on the bone fracture must be converted into compression forces.

The most familiar technique, called tension band-wiring, converts the tensile forces into compression forces by inserting two K-wires across the fracture site and on the tension side of the bone, inserting a cancellous screw into the long bone, and wrapping gauge wire in a figure of eight motion around the head of the screw and the K-wires. The gauge wire is then twisted and pulled to compress the fracture site. This tension band-wiring technique has many disadvantages including, but not limited to, K-wire migration, constructure failure, implant irritation, prominent implants, and common occurrence of implant removal.

Another technique to convert the tensile forces of a bone fracture into compression forces uses two cancellous screws, inserted perpendicular to the fracture site. The main advantage of this technique is the screws can back out of the bone, therefore allowing discontinuation of conversion of the tensile forces into compression forces. However, this can cause gapping of the fracture fragments to recur, requiring a revision surgery to fixate the fracture. Another disadvantage to this technique is the requirement for adequate bone purchase by the screws, which may be difficult if the patient has osteoporotic bone. In addition, the fracture must be fully reduced before implantation, otherwise gapping will occur in the bone fragments and mechanical stability of the fracture will be compromised.

Accordingly, a need exists for new implants and/or systems for treatment of bone fractures, and related methods, that allow for conversion of tensile forces into compressive forces within and/or between various surfaces of a bone fracture while overcoming at least the disadvantages of the tension band-wiring and dual cancellous screw techniques.

SUMMARY

In some embodiments, an orthopedic tension band plate for treatment of a fracture in a bone is provided. The plate includes a proximal portion configured to be disposed against a portion of the bone proximal of the fracture, and a distal portion configured to be disposed against at least a portion of the bone distal of the fracture. The proximal portion includes a first proximal aperture configured to receive a first securing member, and a second proximal aperture disposed distal of the first proximal aperture and configured to receive a second securing member. The distal portion includes a first tine extending distally to a first distal end including a first distal aperture configured to receive a third securing member, and a second tine extending distally to a second distal end including a second distal aperture configured to receive a fourth securing member. At least the first and second tines are configured to wrap around and conform to portions of the bone proximate to the fracture and, thereby, convert tensile forces at the fracture into compressive forces when the third and fourth securing members are driven through the respective first and second distal apertures, into the bone distal of the fracture, the second securing member is secured through the second proximal aperture and into the bone proximal of the fracture, and the first securing member is secured through the first proximal aperture and into the bone proximal of the fracture and proximal of the second securing member.

In some embodiments, a method of utilizing an orthopedic tension band plate for treatment of a fracture in a bone is provided. The method includes disposing at least a portion of the tension band plate proximate to the fracture and against the bone. The tension band plate includes a proximal portion and a distal portion. The proximal portion includes a first proximal aperture configured to receive a first securing member, and a second proximal aperture disposed distal of the first proximal aperture and configured to receive a second securing member. The distal portion includes a first tine extending distally to a first distal end including a first distal aperture configured to receive a third securing member, and a second tine extending distally to a second distal end including a second distal aperture configured to receive a fourth securing member. The method includes driving the third and fourth screws through the respective first and second distal apertures, into the bone distal of the fracture, and perpendicular to and through a plane of the fracture. The method includes driving the first securing member through the first proximal aperture and into the bone proximal of the fracture, thereby causing at least the first and second tines to wrap around and conform to portions of the bone proximate to the fracture, pulling the proximal portion into contact with a portion of the bone proximal of the fracture, and converting tensile forces at the fracture into compressive forces.

In some embodiments, a method of manufacturing an orthopedic tension band plate for treatment of a fracture in a bone is provided. The method includes forming a proximal portion of the tension band plate with a configuration for disposal against a portion of the bone proximal of the fracture at least in that the proximal portion includes a first proximal aperture configured to receive a first securing member, and a second proximal aperture disposed distal of the first proximal aperture and configured to receive a second securing member. The method includes forming a distal portion of the tension band plate with a configuration for disposal against at least a portion of the bone distal of the fracture at least in that the distal portion includes a first tine extending distally to a first distal end including a first distal aperture configured to receive a third securing member, and a second tine extending distally to a second distal end including a second distal aperture configured to receive a fourth securing member. At least the first and second tines are formed with a configuration for wrapping around and conforming to portions of the bone proximate to the fracture and, thereby, a configuration for converting tensile forces at the fracture into compressive forces the third and fourth securing members are secured through the respective first and second distal apertures, into the bone distal of the fracture, the second securing member is secured through the second proximal aperture and into the bone proximal of the fracture, and the first securing member is secured through the first proximal aperture and into the bone proximal of the fracture and proximal of the second securing member.

In some other embodiments, another orthopedic tension band plate for treatment of a fracture in a bone is provided. The plate includes a medial portion comprising an aperture, a proximal portion integrally coupled to one side of the medial portion and a distal portion integrally coupled to an opposite side of the medial portion from the proximal portion. The proximal portion is configured to be disposed against a portion of the bone proximal of the fracture and the distal portion configured to be disposed against at least a portion of the bone distal of the fracture. The distal portion includes a first tine extending distally to a first distal end including a first distal aperture configured to receive a third securing member, and a second tine extending distally to a second distal end including a second distal aperture configured to receive a fourth securing member. The proximal portion includes a first tine extending proximally to a first proximal end including a first proximal aperture configured to receive a third securing member, and a second tine extending proximally to a second proximal end including a second proximal aperture configured to receive a fourth securing member. At least the first and second distal tines are configured to wrap around and conform to portions of the bone proximate to the fracture and, thereby, convert tensile forces at the fracture into compressive forces when the third and fourth securing members are driven through the respective first and second distal apertures, into the bone distal of the fracture, and the first and second securing members are secured through the first and second proximal apertures and into the bone proximal of the fracture.

In some other embodiments, another method of utilizing an orthopedic tension band plate for treatment of a fracture in a bone is provided. The method includes disposing at least a portion of the tension band plate proximate to the fracture and against the bone. The tension band plate includes a medial portion, a proximal portion and a distal portion. The plate includes a medial portion comprising an aperture, a proximal portion integrally coupled to one side of the medial portion and a distal portion integrally coupled to an opposite side of the medial portion from the proximal portion. The proximal portion is configured to be disposed against a portion of the bone proximal of the fracture and the distal portion configured to be disposed against at least a portion of the bone distal of the fracture. The distal portion includes a first tine extending distally to a first distal end including a first distal aperture configured to receive a third securing member, and a second tine extending distally to a second distal end including a second distal aperture configured to receive a fourth securing member. The proximal portion includes a first tine extending proximally to a first proximal end including a first proximal aperture configured to receive a third securing member, and a second tine extending proximally to a second proximal end including a second proximal aperture configured to receive a fourth securing member. At least the first and second distal tines are configured to wrap around and conform to portions of the bone proximate to the fracture and, thereby, convert tensile forces at the fracture into compressive forces when the third and fourth securing members are driven through the respective first and second distal apertures, into the bone distal of the fracture, and the first and second securing members are secured through the first and second proximal apertures and into the bone proximal of the fracture. The method includes driving the third and fourth securing members through the respective first and second distal apertures, into the bone distal of the fracture, and perpendicular to and through a plane of the fracture. The method includes driving the first and second securing members through the respective first and second distal apertures, into the bone distal of the fracture, thereby causing at least the first and second tines of the distal portion to wrap around and conform to portions of the bone proximate to the fracture, pulling the proximal portion into contact with a portion of the bone proximal of the fracture, and converting tensile forces at the fracture into compressive forces.

In some embodiments, a method of manufacturing an orthopedic tension band plate for treatment of a fracture in a bone is provided. The method includes forming a medial portion comprising an aperture and integrally forming a proximal portion with a configuration for disposal against a portion of the bone proximal of the fracture, The proximal portion comprises a first proximal tine extending distally to a first proximal end comprising a first proximal aperture configured to receive a first securing member, and a second proximal tine extending proximally to a second proximal end comprising a second proximal aperture configured to receive a second securing member. The method includes integrally forming the distal portion of the tension band plate with a configuration for disposal against at least a portion of the bone distal of the fracture at least in that the distal portion comprises a first tine extending distally to a first distal end comprising a first distal aperture configured to receive a third securing member, and a second tine extending distally to a second distal end comprising a second distal aperture configured to receive a fourth securing member.

BRIEF DESCRIPTION OF THE DRAWINGS

A more complete appreciation of the subject matter of the present disclosure and of the various advantages thereof can be realized by reference to the following detailed description in which reference is made to the accompanying drawings in which.

DETAILED DESCRIPTION

Implementations of the technology described herein are directed generally to implants and/or systems for treatment of bone fractures and associated methods. The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Figure 1B:
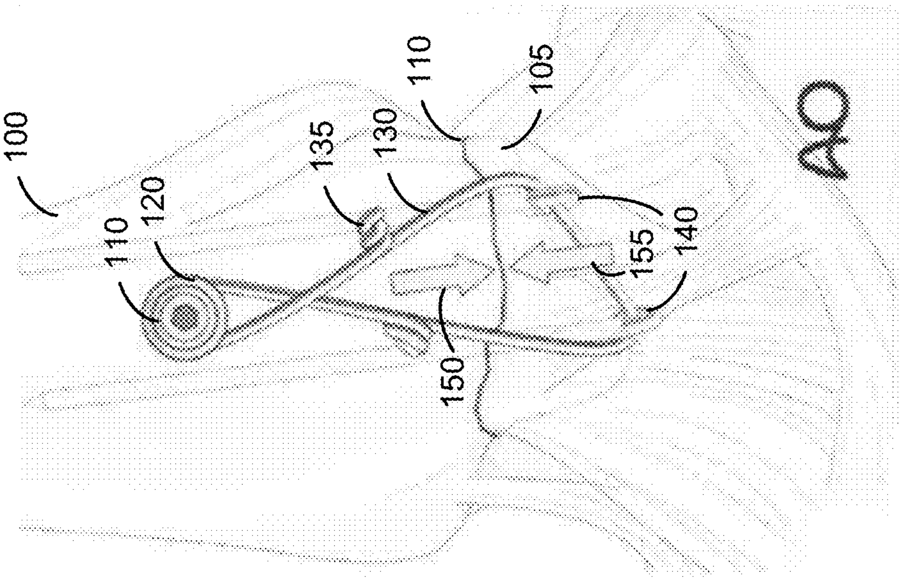
FIG. 1B illustrates a second view of the medial malleolar fracture stabilized using tension band wiring that is perpendicular to the first view of FIG. 1A.
Figure 1A:
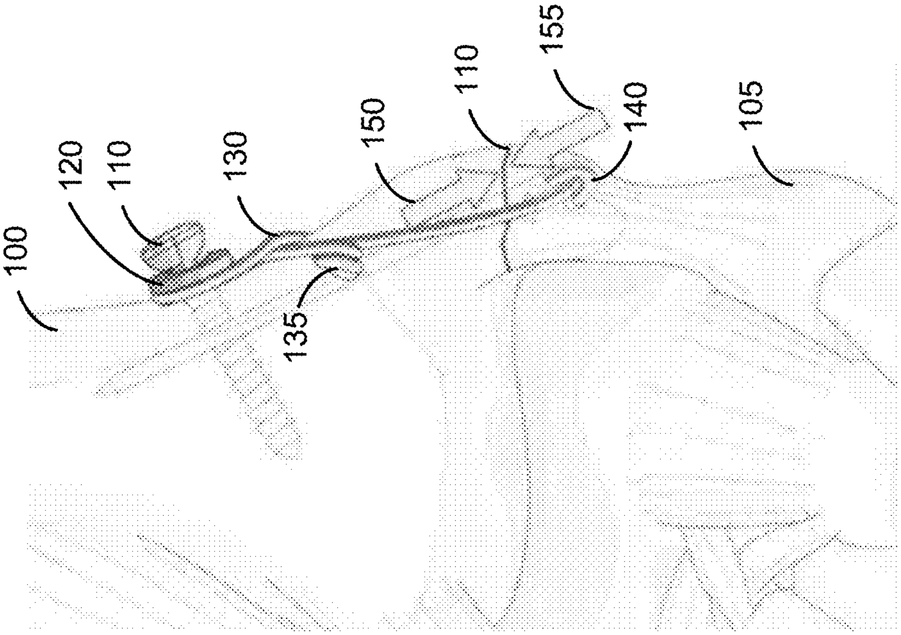
FIG. 1A illustrates a first view of a medial malleolar fracture of a patient stabilized using tension band wiring, in accordance with some example embodiments.

FIGS. 1A and 1B illustrate first and second views of a medial malleolar fracture 110 of a patient stabilized using tension band wiring 130, in accordance with some example embodiments. Such tension banding techniques are often used on avulsion and transverse fracture patterns of the medial malleolus 100 (i.e., of the tibia), though the application of tension banding techniques are not limited to such fractures and/or fracture patterns. However, when such fracture patterns do occur, surgeons will often place two partially threaded cancellous bone screws through the fracture to achieve compression. However, studies have found that tension banding techniques, such as those illustrated in FIGS. 1A and 1B, are stronger than screw fixation in resisting clinical failure (e.g., greater than 2 mm of fracture displacement).

In FIGS. 1A and 1B, medial malleoli 100 are illustrated as having a distal fragment or section of bone 105 defined by fracture 110. Fracture 110 is shown after having been completely reduced. Two Kirshner wires (K-wires) 140 are driven into distal fragment or section of bone 105 through and across fracture 110 on the tension side of bone 100. A washer 120 is inserted over threads of a cancellous bone screw 110 and screw 110 is driven into the long bone of medial malleoli 100 approximately 2 to 3 cm above (e.g., proximal of) fracture 110. Gauge wire 130 is wrapped around the head of screw 110 and around or through protruding portions of K-wires 140 in a "figure eight" motion. Gauge wire 130 is then twisted 135 and pulled to compress fracture 110. Opposite compressive forces 150 and 155 are illustrated on either side of fracture 110.

This disclosure provides implants and/or systems for treatment of foot and/or ankle fractures, and associated methods, which convert tensile forces of fractures to compression forces, while avoiding the disadvantages of the tensioning techniques previously described. Tension band plate 200 of this system is designed to mimic the tension banding technique of FIGS. 1A and 1B, however, utilizing fewer components and/or fewer steps. Accordingly, tension plate 200 is designed with at least one goal of modernizing the K-wire tension band technique described in connection with FIGS. 1A and 1B.

Example Embodiments

Figure 2:
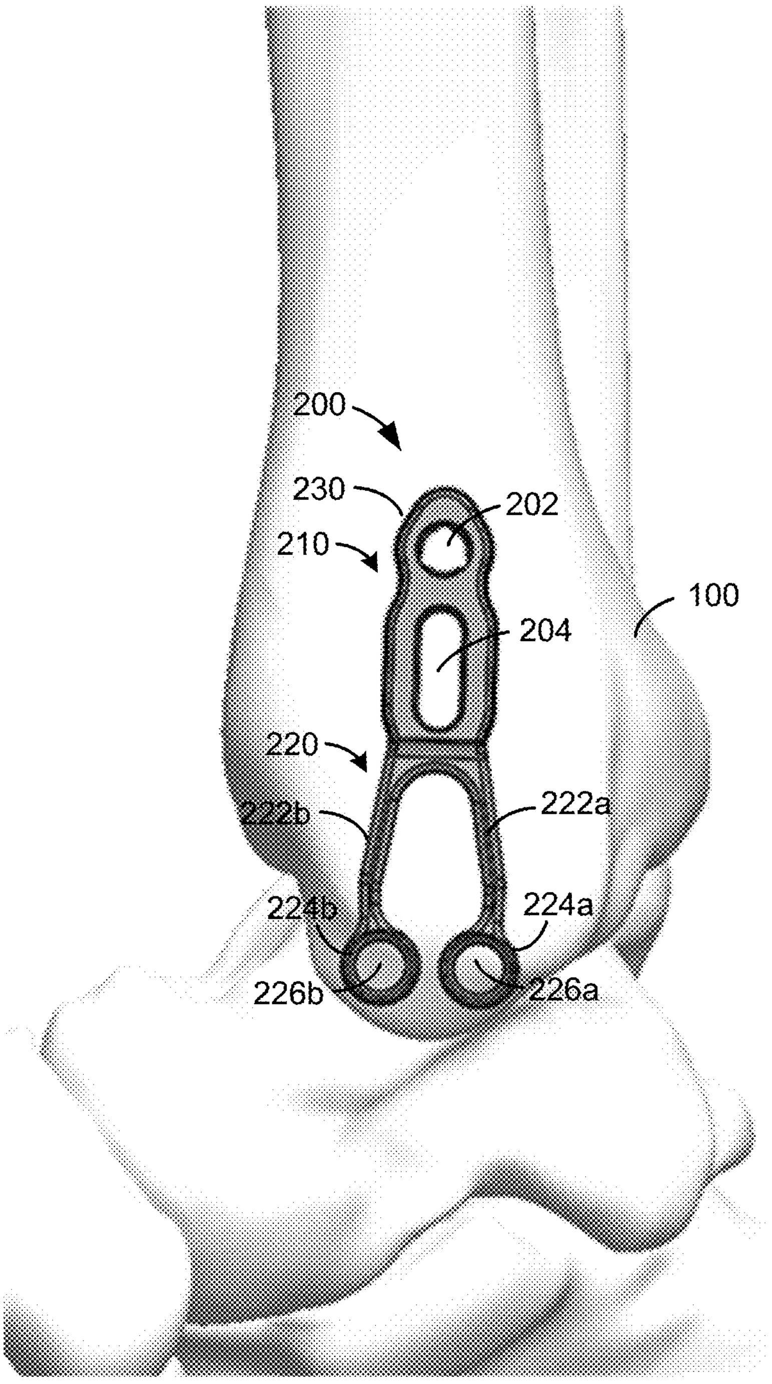
FIG. 2 illustrates a tension band plate disposed on a distal portion of a medial malleolus of a patient, in accordance with some example embodiments.
Figure 3:
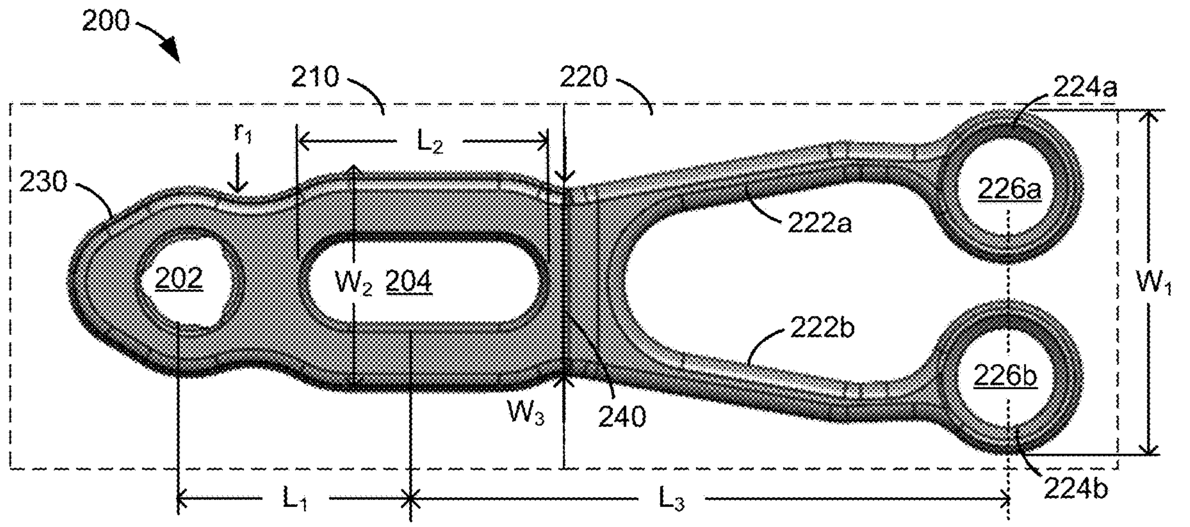
FIG. 3 illustrates a top view of the tension band plate of FIG. 2, in accordance with some example embodiments.
Figure 4:
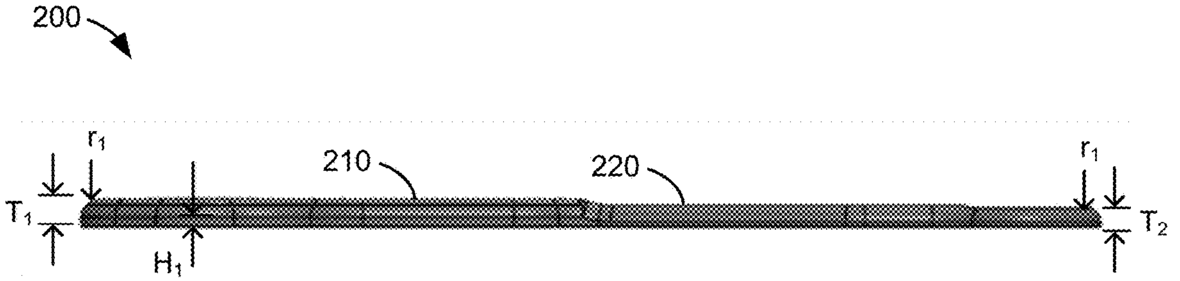
FIG. 4 illustrates a side view of the tension band plate of FIG. 2, in accordance with some example embodiments.
Figure 5:
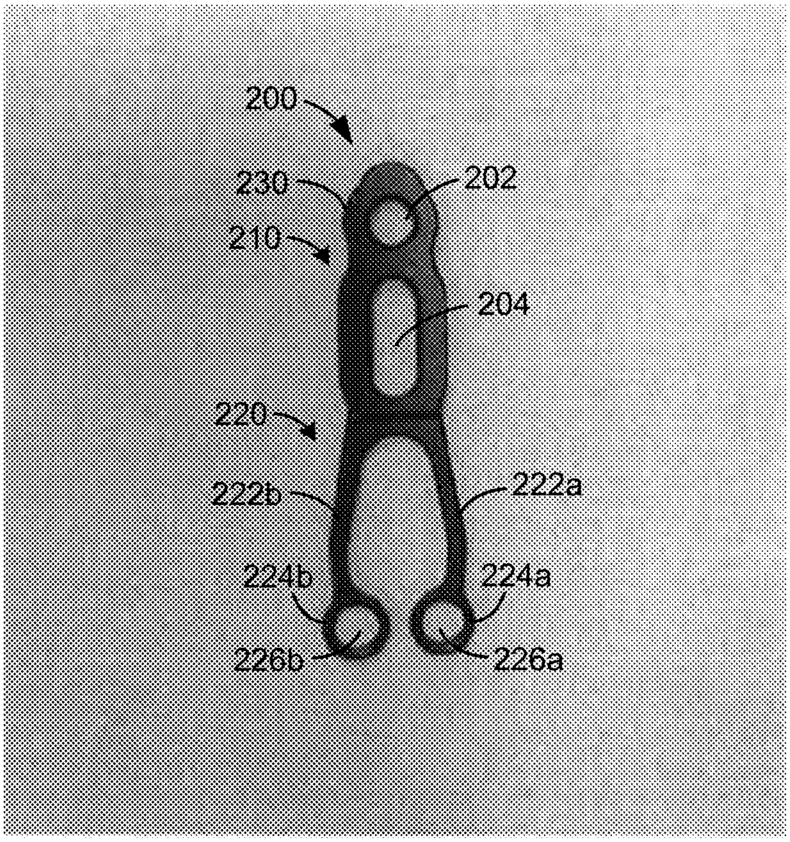
FIG. 5 is photograph of a top view of the tension band plate of FIG. 2, in accordance with some example embodiments.
Figure 6:
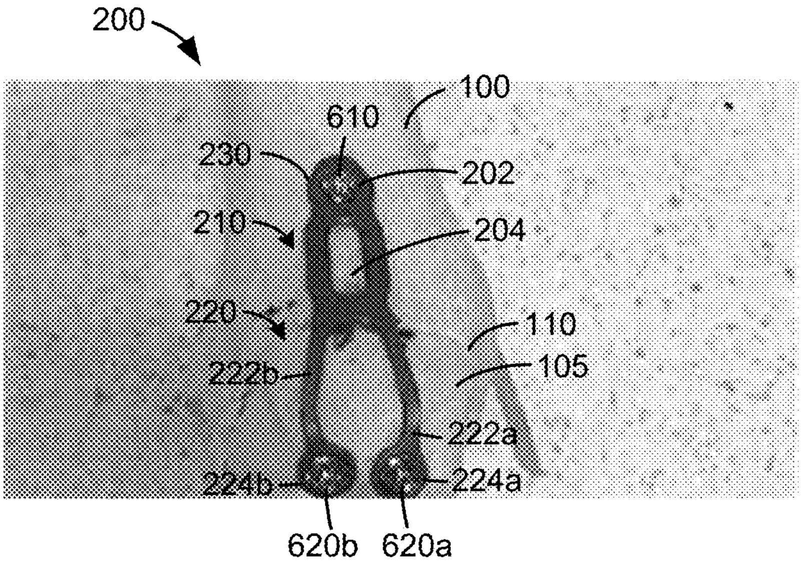
FIG. 6 is photograph of a first view of the tension band plate of FIG. 5 coupled to a distal portion of a medial malleolus of a patient, in accordance with some example embodiments.
Figure 7:
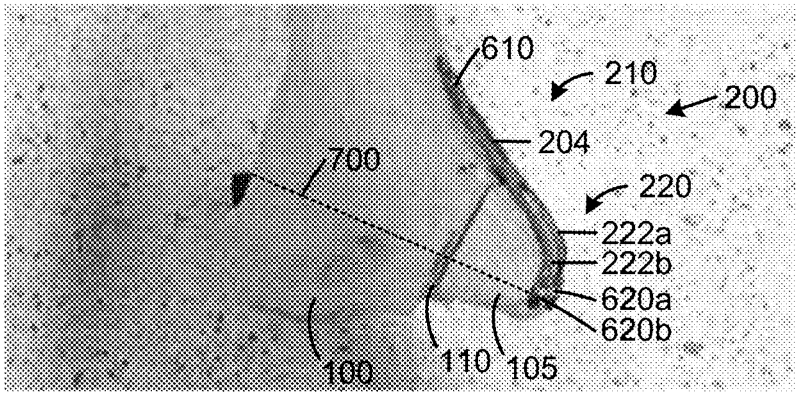
FIG. 7 is photograph of a second view of the tension band plate of FIG. 5 coupled to the distal portion of the medial malleolus of the patient that is perpendicular to the first view of FIG. 6.

FIGS. 2-7 and 10-11 illustrate tension band plates 200, 1000 of the disclosed system, configured for use to fractures 110 on medial malleolus 100. FIG. 2 illustrates tension band plate 200 on a right tibia 100 of a $50^{th}$ percentile male. FIG. 3 illustrates a top view of tension band plate 200. FIG. 4 illustrates a side view of tension band plate 200. FIG. 5 is a photograph of tension band plate 200 substantially as shown in FIG. 3. FIG. 6 is a photograph of a first view of tension band plate 200 disposed on right tibia 100 similar to that shown in FIG. 2. And FIG. 7 illustrates a second view, perpendicular to the first view of FIG. 6, of tension band plate 200 disposed on right tibia 100. Tension band plate 200 will now be described in more detail in connection with one or more of FIGS. 2-7. An alternative embodiment of plate 200 are also described in connection with at least FIGS. 10-11.

Tension band plate 200 comprises a proximal portion 210 and a distal portion 220. Proximal portion 210 is configured to be disposed on and/or against a portion of bone 100 proximal of fracture 110. Distal portion 220 is configured to be disposed on and/or against at least portions of bone 105 distal of fracture 110.

Proximal portion 210 comprises a first proximal aperture 202 configured to receive a first securing member 610 (see FIGS. 6 and 7). In some embodiments, first proximal aperture 202 has a substantially circular shape and/or beveled or otherwise rounded edges. In some embodiments, first securing member 610 comprises one of a bone screw, a pin, a wire or a post. securing member. Accordingly, in some embodiments, first securing member 610 is configured to be driven into the long bone of malleoli 100 proximal (e.g., 2 to 3 cm) of fracture 110.

Proximal portion 210 comprises a second proximal aperture 204 disposed distal of first proximal aperture 202. In some embodiments, first proximal aperture 202 and/or second proximal aperture 204 comprises a combination compression/gliding aperture. In some embodiments, either or both of apertures 202, 204 may comprise a locking compression/gliding hole. In some embodiments, either or both of apertures 202, 204 may comprise a standard locking hole.

In some embodiments, second proximal aperture 204 is configured to receive a second securing member (not shown) similar to first securing member 610. In some embodiments, second proximal aperture 204 is disposed along a centerline of plate 200 extending longitudinally through proximal and distal portions 210, 220. In some embodiments, second proximal aperture 204 has an elongated shape, for example a rectangle having parallel long sides and convex semicircles (e.g., bowing outward) for the short sides. In some embodiments, second proximal aperture 204 has a length $L_2$ of 7.11 mm to provide extra compression if needed or desired. In some embodiments, a spacing $L_1$ between first proximal aperture 202 and second proximal aperture 204 is approximately 7.62 mm.

Distal portion 220 comprises a first extension or tine **222*a* extending distally, and in some cases slightly outwardly or laterally to one side of and compared to the longitudinal centerline. Distal portion 220 comprises a second extension or tine 222*b* extending distally, and in some cases slightly outwardly or laterally to an opposite side of and compared to the longitudinal centerline. In some embodiments, a proximal portion of extensions or tines 222*a*,222*b* have a slight (e.g., 10-degree) bend in the lateral direction to decrease palpability of extensions or tines 222***a*,222*b*. In some such embodiments, extensions or tines 222*a*,222*b* then angle back in (e.g., a bend in the medial direction by 5 degrees) to "hug" or conform to an underlying shape of a portion of the bone being reduced and/or stabilized, e.g., medial malleolus 100, when placed in tension, which would not occur if extensions or tines 222*a*,222*b* extended straight away distally of proximal portion 210.

Extensions or tines 222*a*, 222*b* comprise respective first and second distal apertures 226*a*, 226*b* disposed within respective distal ends 224*a*, 224*b* of first and second extensions or tines 222*a*, 222*b*. Similar to first and second proximal apertures 202, 204, first and second distal apertures 226*a*, 226*b* each comprise a combination compression/gliding aperture. In some embodiments, either or both of apertures 226*a*, 226*b* may comprise a locking compression/gliding hole. In some embodiments, either or both of apertures 226*a*, 226*b* may comprise a standard locking hole.

First and second distal apertures 226*a*, 226*b* are configured to receive respective third and fourth securing members 620*a*, 620*b*. In some embodiments, third and fourth members 620*a*, 620*b* may each comprise one of a bone screw, a pin, a wire or a post. Accordingly, in some embodiments, third and/or fourth securing members 620*a*, 620*b* may be configured to be driven into bone 105 perpendicular to a plane of fracture 110. In some embodiments, a longitudinal spacing $L_3$ between second proximal aperture 204 and each of first and second distal apertures 226*a*, 226*b* is approximately 23.6 mm.

Spacings between apertures of plate 200 are designed to adequately capture the fracture of the bone(s) being reduced and/or stabilized. In some such applications, such fracture(s) may comprise and/or involve a distal avulsion fragment 105 and proximal bone 100. While particular spacings and/or dimensions are provided for one or more features of plate 200, the present disclosure is not so limited and any suitable spacings and/or dimensions are also contemplated.

Although medial malleolus 100 of the tibia endures significant axial forces, tension band plate 200 does not need to be able to withstand these forces because the plate is only designed to convert the tensile forces caused from fractures into compression forces. The same applies to torsional requirements of tension band plate 200. Accordingly, plate 200 may be made to have a substantially reduced thickness(es) compared to other plates and/or ankle stabilization offerings.

However, one of the considerations taken into account when designing tension band plate 200 is the prominent distal end of medial malleolus 100. Accordingly, tension plate 200 has a varying thickness, for example, a thickness $T_1$ of 1.3 mm along proximal portion 210 of plate 200 and a thickness $T_2$ of 1.0 mm along distal portion 220 of plate 200 (e.g., along extensions and/or tines 222*a*, 222*b* and distal apertures 226*a*, 226*b*). Thickness $T_2$ of 1.0 mm allows extensions and/or tines 222*a*, 222*b* to be easily and manually bent by the surgeon to match the contour of medial malleolus 100. However, it is also important to ensure extensions and/or tines 222*a*, 222*b* will not break while being bent. Extensions and/or tines 222*a*, 222*b* are thus designed to be bent, for example with bending pliers, multiple times without breaking.

The varying thicknesses, e.g., $T_1$ and $T_2$, minimizes plate palpability and irritation, especially at the distal tip of the tibia where plate irritation commonly occurs, and can ultimately lead to decreased implant removal. Plate 200 eliminates a significant problem of high palpability and patient irritation with the current K-wire tension band techniques. This provides a particularly valuable proposition for the treatment of ankle fractures in the geriatric and/or osteopenic/osteoporotic patient population.

Tension band plate 200 may also comprise an edge profile (e.g., a perimeter) having a straight height $H_1$ of 0.48 mm (e.g., a substantially vertical side extending from a bottom edge of tension band plate 200) and a rounded upper edge having a radius of curvature $r_1$ of 0.76 mm continuing from a top of the substantially vertical side. Such dimensions (e.g., at least $H_1$ and $r_1$) give plate 200 a smooth vanishing edge that minimizes irritation and palpability. Since plate 200 is designed to be manipulated and bent, it does not have any curvature to specific anatomy (e.g., plate 200 is substantially flat). Such a substantially flat form also decreases the cost of manufacturing plate 200.

A maximum width $W_2$ of proximal portion 210 is 10.16 mm. A minimum width $W_3$ of proximal portion 210 (e.g., at a scalloped portion 240 separating or defining a border between first and second portions 210, 220) is 7.91 mm. A difference between $W_2$ and $W_3$ allows for easy adaptation of the contouring of plate 200 while plate 200 is being sucked or pulled down against the patient specific anatomy. A maximum width $W_1$ of distal portion 220 of plate 200 is about 14.5 mm. In some embodiments, maximum width $W_1$ is selected based on the size of the distal portion of medial malleolus 100 such that the selection still allows third and fourth securing members 620*a*, 620*b* to be secured to (and/or driven into) bone fragment 105, perpendicular to and through the plane of fracture 110 and into medial malleolus 100.

In yet other embodiments, distal portion 1020 of plate 1000 may comprise just one of tines 1022*a*, 1022*b*. Likewise, in some embodiments, proximal portion 1010 of plate 1000 may comprise just one of tines 1022*c*, 1022*d*.

In some embodiments, rather than comprising a single aperture, one or more of apertures 202, 204, 226*a*, 226*b* may each comprise a plurality of apertures, each configured to receive a respective securing member. Such embodiments may allow for even more advanced molding of plate 200 to the patient-specific anatomy.

In some embodiments, tension band plate 200 may only be offered in one overall length at least because adequate fixation of avulsion fractures of medial malleolus 100 can be achieved with fixation points provided by tension band plate 200.

Figure 10:
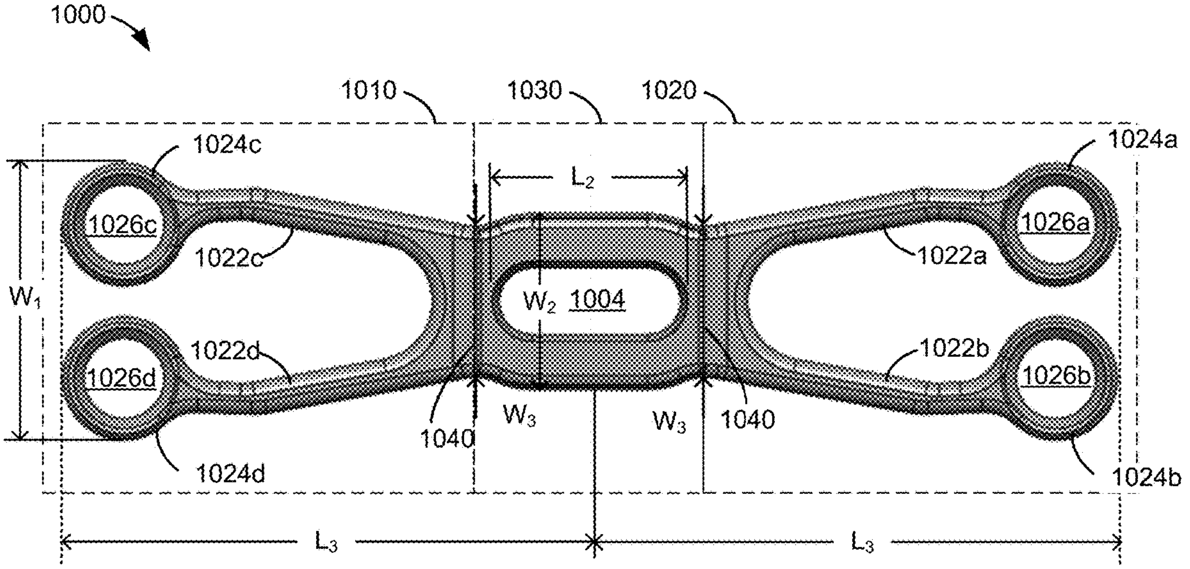
FIG. 10 illustrates a top view of another tension band plate, in accordance with some example embodiments.
Figure 11:
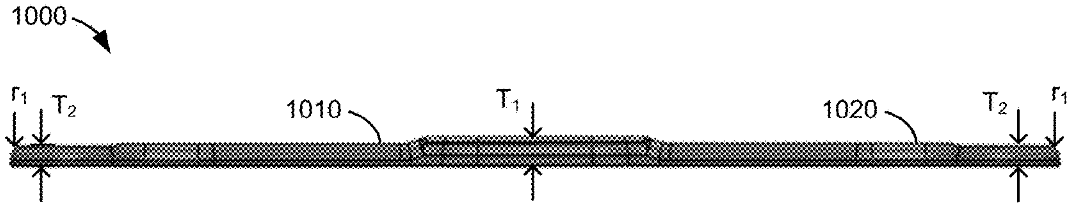
FIG. 11 illustrates a side view of the tension band plate of FIG. 10, in accordance with some example embodiments.

An alternative embodiment of tension band plate 200, tension band plate 1000, is illustrated in FIGS. 10 and 11. Tension band plate 1000 is substantially a symmetrical mirror image of the portion of plate 200 distal of the midline of second proximal aperture 204 along the proximal-distal centerline of plate 200.

Accordingly, plate 1000 comprises a proximal portion 1010, a medial portion 1030, and a distal portion 1020. Proximal portion 1010 is configured to be disposed on and/or against a portion of bone 100 proximal of fracture 110. Distal portion 1020 is configured to be disposed on and/or against at least portions of bone 105 distal of fracture 110. Medial portion 1030 is disposed between proximal and distal portions 1010, 1020.

Medial portion 1030 comprises a medial aperture 1004, which may substantially correspond to second proximal aperture 204 as previously described anywhere in this disclosure. Medial aperture 1004 may be disposed along a centerline of plate 1000 extending longitudinally through proximal, medial and distal portions 1010, 1030, 1020. Medial aperture 1004 is configured to receive a securing member (not shown) similar to first securing member 610 as previously described anywhere in this disclosure.

Proximal portion 1010 comprises a first proximal extension or tine 1022*c* extending distally, and in some cases slightly outwardly or laterally to one side of and compared to the longitudinal centerline. Proximal portion 1010 comprises a second extension or tine 1022*d* extending distally, and in some cases slightly outwardly or laterally to an opposite side of and compared to the longitudinal centerline. In some embodiments, a distal portion of extensions or tines 1022*c*,1022*d* have a slight (e.g., 10-degree) bend in the lateral direction to decrease palpability of extensions or tines 1022*c*,1022*d*. In some such embodiments, extensions or tines 1022*c*,1022*d* then angle back in (e.g., a bend in the medial direction by 5 degrees) to "hug" or conform to an underlying shape of a portion of the bone being reduced and/or stabilized when placed in tension, which would not occur if extensions or tines 1022*c*,1022*d* extended straight away distally of proximal portion 1010.

Extensions or tines 1022*c*, 1022*d* comprise respective first and second proximal apertures 1026*c*, 1026*d* disposed within respective proximal ends 1024*c*, 1024*d* of first and second proximal extensions or tines 1022*c*, 1022*d*. In some embodiments, first and second proximal apertures 1026*c*, 1026*d* each comprise a combination compression/gliding aperture, a locking compression/gliding hole or a standard locking hole.

First and second proximal apertures 1026*c*, 1026*d* are configured to receive respective first and second securing members (which are similar to securing members 620*a*, 620*b* as previously described in connection with plate 200). In some embodiments, these first and second securing members may each comprise one of a bone screw, a pin, a wire or a post. Accordingly, in some embodiments, first and second securing members may be configured to be driven into bone perpendicular to a plane of the fracture. In some embodiments, a longitudinal spacing $L_3$ between medial aperture 1004 and each of first and second proximal apertures 1026*c*, 1026*d* is approximately 103.6 mm. While particular spacings and/or dimensions are provided for one or more features of plate 1000, the present disclosure is not so limited and any suitable spacings and/or dimensions are also contemplated.

Distal portion 1020 comprises a first distal extension or tine 1022*a* extending distally, and in some cases slightly outwardly or laterally to one side of and compared to the longitudinal centerline. Distal portion 1020 comprises a second extension or tine 1022*b* extending distally, and in some cases slightly outwardly or laterally to an opposite side of and compared to the longitudinal centerline. In some embodiments, a proximal portion of extensions or tines 1022*a*,222*b* have a slight (e.g., 10-degree) bend in the lateral direction to decrease palpability of extensions or tines 1022*a*,222*b*. In some such embodiments, extensions or tines 1022*a*,222*b* then angle back in (e.g., a bend in the medial direction by 5 degrees) to "hug" or conform to an underlying shape of a portion of the bone being reduced and/or stabilized, e.g., medial malleolus 100, when placed in tension, which would not occur if extensions or tines 1022*a*,222*b* extended straight away distally of proximal portion 1010.

Extensions or tines 1022*a*, 1022*b* comprise respective first and second distal apertures 1026*a*, 1026*b* disposed within respective distal ends 1024*a*, 1024*b* of first and second extensions or tines 1022*a*, 1022*b*. In some embodiments, first and second distal apertures 1026*a*, 1026*b* each comprise a combination compression/gliding aperture, a locking compression/gliding hole or a standard locking hole.

First and second distal apertures 1026*a*, 1026*b* are configured to receive respective third and fourth securing members 620*a*, 620*b* as previously described in connection with plate 200. In some embodiments, third and fourth members 620*a*, 620*b* may each comprise one of a bone screw, a pin, a wire or a post. Accordingly, in some embodiments, third and/or fourth securing members 620*a*, 620*b* may be configured to be driven into bone 105 perpendicular to a plane of fracture 110. In some embodiments, a longitudinal spacing $L_3$ between medial aperture 1004 and each of first and second distal apertures 1026*a*, 1026*b* is approximately 103.6 mm. While particular spacings and/or dimensions are provided for one or more features of plate 1000, the present disclosure is not so limited and any suitable spacings and/or dimensions are also contemplated.

Tension plate 1000 has a varying thickness, for example, a thickness $T_1$ of 1.3 mm along medial portion 1030 of plate 1000 and a thickness $T_2$ of 1.0 mm along proximal portion 1010 and distal portion 1020 of plate 1000 (e.g., along extensions and/or tines 1022*a*, 1022*b*, 1022*c*, 1022*d* and apertures 1026*a*, 1026*b*, 1026*c*, 1026*d*). Thickness $T_2$ of 1.0 mm allows extensions and/or tines 1022*a*, 1022*b*, 1022*c*, 1022*d* to be easily and manually bent by the surgeon to match the contour of the bone.

Tension band plate 1000 may also comprise an edge profile (e.g., a perimeter) having a straight height $H_1$ of 0.48 mm (e.g., a substantially vertical side extending from a bottom edge of tension band plate 1000) and a rounded upper edge having a radius of curvature $r_1$ of 0.76 mm continuing from a top of the substantially vertical side. Such dimensions (e.g., at least $H_1$ and $r_1$) give plate 1000 a smooth vanishing edge that minimizes irritation and palpability. Since plate 1000 is designed to be manipulated and bent, it does not have any curvature to specific anatomy (e.g., plate 1000 is substantially flat). Such a substantially flat form also decreases the cost of manufacturing plate 1000.

The maximum width $W_2$ of medial portion 1030 is 10.16 mm. The minimum width $W_3$ of proximal portion 1010 (e.g., at a scalloped portion 1040 separating or defining a border between each of first and second portions 1010, 1020 and medial portion 1030) is 7.91 mm. The difference between $W_2$ and $W_3$ allows for easy adaptation of the contouring of plate 1000 while plate 1000 is being sucked or pulled down against the patient specific anatomy. A maximum width $W_1$ of each of proximal portion 1010 and of distal portion 1020 of plate 1000 is about 14.5 mm.

In yet other embodiments, distal portion 1020 of plate 1000 may comprise just one of tines 1022*a*, 1022*b*. Similarly, in in some embodiments, proximal portion 1010 of plate 1000 may comprise just one of tines 1022*c*, 1022*d*.

In some embodiments, rather than comprising a single aperture, one or more of apertures 1040, 1026*a*, 1026*b*, 1026*c*, 1026*d* may each comprise a plurality of apertures, each configured to receive a respective securing member. Such embodiments may allow for even more advanced molding of plate 1000 to the patient-specific anatomy. Several procedures involving tension band plate 200 and/or 1000 will now be described with respect to FIGS. 2-7 and 10-11. In some embodiments, tension band plate 200, 1000 is disposed on the tensile side of bone 100. Plate 200, 1000 may provide tension using either of several example implantation procedures.

In a first example implantation procedure, tension band plate 200, 1000 creates tension by inserting securing members 620*a*, 620*b* into distal apertures 226*a*, 226*b*, 1026*a*, 1026*b* at distal ends 224*a*, 224*b* 1024*a*, 1024*b* of extensions or tines 222*a*, 222*b*, 1022*a*, 1022*b* of plate 200, 1000 (see, FIGS. 6 and 7). Securing members 620*a*, 620*b* are secured to (and/or drive into) bone fragment 105 perpendicular to and through a plane of fracture 110, and into bone 100. Plate 200, 1000 is provided unbent, thereby causing proximal portion 210, 1010 of plate 200, 1000 to protrude away from bone 100 once securing members 620*a*, 620*b* are inserted.

In some embodiments, where additional compression of fracture 110 is desired, a securing member (e.g., a non-locking screw) (not shown) may optionally be inserted into second proximal aperture 204 (or aperture 1004 of plate 1000) and secured to (and/or driven into) bone 100. Finally, first securing member 610 may be inserted into proximal aperture 202 in proximal portion 210 of plate 200 (or respective securing members may be inserted into corresponding apertures 1026*c*, 1026*d*). Since plate 200, 1000 is provided unbent, securing and/or driving such a securing member through aperture 204, 1004 and/or securing member 610 through aperture 202 (or respective securing members through corresponding apertures 1026*c*, 1026*d*) and into bone 100 causes extensions or tines 222*a*, 222*b* (1022*a*, 1022*b*) to wrap around the distal portion of medial malleolus 100, 105 and creates tension as plate 200, 1000 is pulled down onto bone 110, thereby converting tensile forces into compressive forces similar to 150, 155 of FIGS. 1A, 1B.

A second procedure to create tension may comprise first inserting the securing member (not shown) through second proximal aperture 204 (or aperture 1004 for plate 1000) and into bone 100, then inserting third and fourth securing members 620*a*, 620*b* through apertures 226*a*, 226*b*, 1026*a*, 1026*b* and into bone fragment 105 perpendicular to and through a plane of fracture 110, and into bone 100, followed by inserting first securing member 610 into first proximal aperture 202 of plate 200 (or respective securing members through corresponding apertures 1026*c*, 1026*d*). As above, since plate 200 is provided unbent, driving securing member 610 through aperture 202 (or respective securing members through corresponding apertures 1026*c*, 1026*d*) and into bone 100 and/or securing members 620*a*, 620*b* through apertures 226*a*, 226*b*, 1026*a*, 1026*b* and into bone 105 causes extensions or tines 222*a*, 222*b*, 1022*a*, 1022*b* to wrap around the distal portion of medial malleolus 100, 105 and creates tension as plate 200, 1000 is sucked or pulled down onto bone 110, thereby converting tensile forces into compressive forces similar to 150, 155 of FIGS. 1A, 1B.

In some embodiments, a system comprising tension band plate 200, 1000 provides a solution for treatment of tri-malleolar fractures as well as a solution for treatment of Danis-Weber fractures.

The described tension band plate 200, 1000 is also advantageous because fracture 110 need not be reduced prior to implantation of tension band plate 200, 1000. Since band plate 200, 1000 is provided unbent, reduction of fracture 110 will occur as second proximal aperture 204 (or aperture 1004) is used, and/or as the remaining securing members are tightened, thereby pulling plate 200, 1000 down onto bone 100, 105.

Example Method(s) of Use

Figure 8:
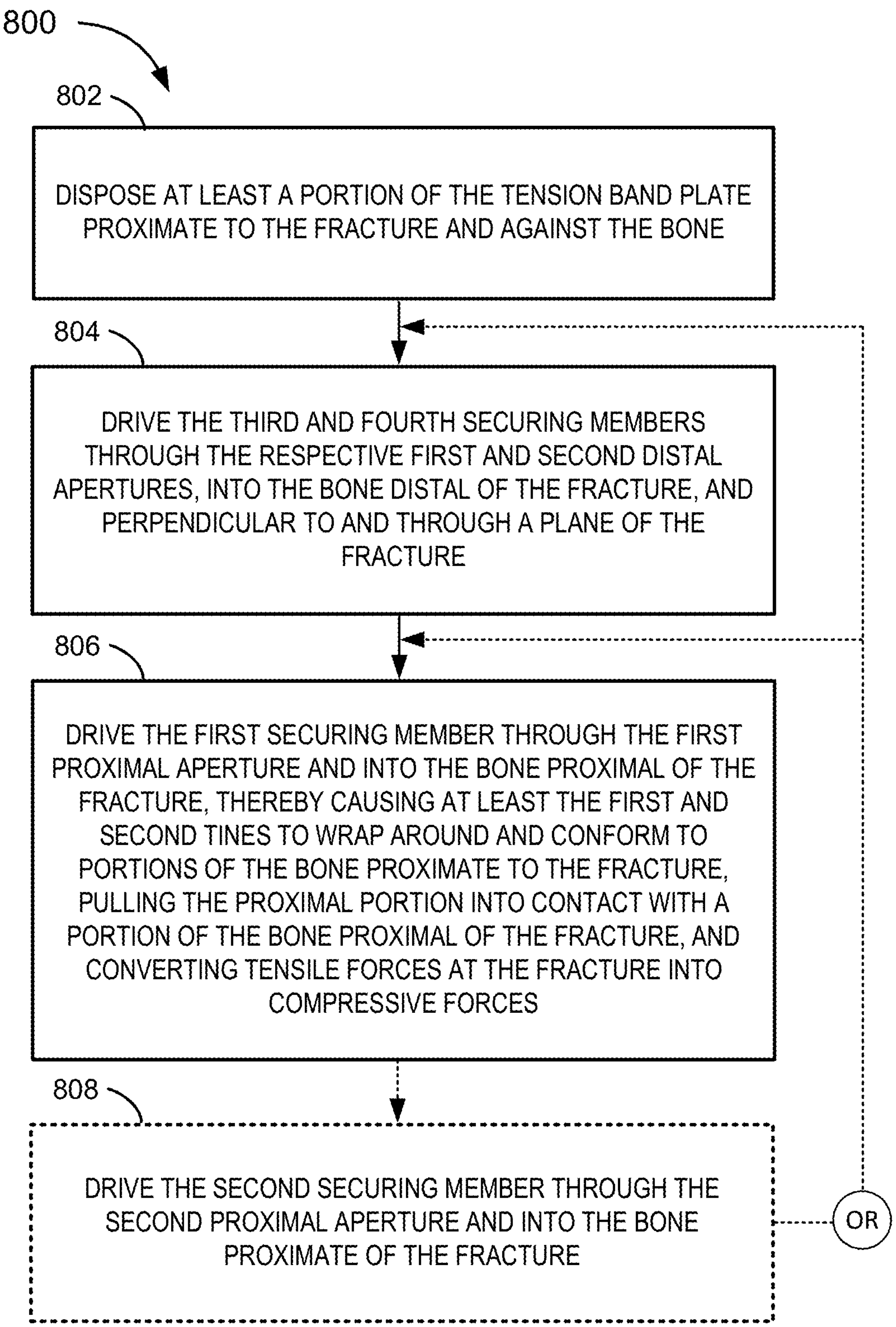
FIG. 8 illustrates a flowchart related to a method of using a tension band plate to treat bone fractures, in accordance with some example embodiments.

The disclosure now turns to FIG. 8 and one or more example methods of using a tension band plate to treat tibial fractures, as described anywhere in this disclosure. Although particular steps are described herein, the present application is not so limited and alternative methods may include a subset of these steps, in the same or different order, and may additionally include one or more additional steps not described herein.

Step 802 includes disposing at least a portion of the tension band plate proximate to the fracture and against the bone. For example, as previously described in connection with at least FIGS. 2-7, a surgeon may dispose at least a portion of tension band plate 200 proximate to fracture 110 and against bone 100, 105. In some embodiments, the portion disposed against the bone may be one or both of first and second distal apertures 226*a*, 226*b* in preparation of securing third and fourth securing members 622*a*, 622*b* therethrough and to the bone. As previously described, tension band plate 200 comprises a proximal portion 210 and a distal portion 220. Proximal portion includes first proximal aperture 202 configured to receive first securing member 610 and second proximal aperture 204 disposed distal of first proximal aperture 202 and configured to receive a second securing member (e.g., a non-locking screw) (not shown). Distal portion 220 includes first tine 220*a* extending distally to first distal end 224*a* comprising first distal aperture 226*a* configured to receive third securing member 620*a*, and second tine 222*b* extending distally to second distal end 224*b* comprising second distal aperture 226*b* configured to receive fourth securing member 620*b*. Step 802 may also be carried out utilizing plate 1000 of FIGS. 10 and 11 and its corresponding elements.

Step 804 includes driving the third and fourth securing members through the respective first and second distal apertures, into the bone distal of the fracture, and perpendicular to and through a plane of the fracture. For example, as previously described in connection with at least FIGS. 2-7, the surgeon may drive third and fourth securing members 620*a*, 620*b* through respective first and second distal apertures 226*a*, 226*b* into bone 105 distal of fracture 110, and perpendicular to and through a plane of fracture 110. Step 804 may also be carried out as described utilizing plate 1000 of FIGS. 10 and 11 and its corresponding elements.

Step 806 includes driving the first securing member through the proximal aperture and into the bone proximal of the fracture, thereby causing at least the first and second tines to wrap around and conform to portions of the bone proximate to the fracture, pulling the proximal portion into contact with a portion of the bone proximal of the fracture, and converting tensile forces at the fracture into compressive forces. For example, as previously described in connection with at least FIGS. 2-7, the surgeon may drive first securing member 610 through first proximal aperture 202 and into bone 100 proximal of fracture 110, thereby causing at least first and second tines 222*a*, 222*b* to wrap around and conform to portions of bone 100,105 proximate to fracture 110, pulling proximal portion 210 into contact with a portion of bone 100 proximal of fracture 110, and converting tensile forces at fracture 110 into stabilizing, compressive forces.

Where step 806 is carried out utilizing plate 1000, the step may include driving a first securing member through first proximal aperture 1026*c* and into the bone proximal of the fracture and a second securing member through second proximal aperture 1026*c* and into the bone proximal of the fracture, thereby causing at least the first and second tines of each of the proximal and distal portions to wrap around and conform to portions of the bone proximate to the fracture, pulling the proximal portion into contact with a portion of the bone proximal of the fracture, and converting tensile forces at the fracture into compressive forces.

In some embodiments, flowchart 800 may include a step 808, including driving the second securing member through the second proximal aperture and into the bone proximate of the fracture. While step 808 is illustrated after step 806, the present disclosure contemplates also performing step 808 after step 802 and before step 804 or, alternatively, after step 804 and before step 806.

For example and not limitation, as previously described in connection with at least FIGS. 2-7, in a first example procedure, where additional compression of fracture 110 is desired (for example where reduction is accomplished by implantation of plate 200 itself), a second securing member (not shown but similar to first securing member 610) may be secured through second proximal aperture 204 and into bone 100 proximate of fracture 110 after driving third and fourth securing members into bone fragment 105 perpendicular to, and through, the plane of fracture 110 and into bone 100, but before driving first securing member 610 into bone 100 proximal of fracture 110.

For further example and not limitation, as previously described in connection with at least FIGS. 2-7, in a second example procedure, the second securing member (not shown) may be secured through second proximal aperture 204 and into bone 100 proximate of fracture 110 before driving third and fourth securing members into bone fragment 105 perpendicular to, and through, the plane of fracture 110 and into bone 100, which may occur before driving first securing member 610 into bone 100 proximal of fracture 110.

Where step 808 is carried out utilizing plate 1000, the step would correspond to driving a fifth securing member though medial aperture 1004, which corresponds to second proximal aperture 204 of plate 200.

In some embodiments, a method related to flowchart 800 may include automatically reducing fracture 110 by driving first, second third, and fourth securing members 610, 620*a*, 620*b* into the respective portions of bone 100, 105 while at least a portion of tension band plate 200 is disposed against the portions of bone 100, 105 proximate to unreduced fracture 110 and as at least a portion of tension band plate 200 conforms to the portions of bone 100,105 proximate to fracture 110.

Where the reducing step is carried out utilizing plate 1000, the step would correspond to driving the first through fifth securing members through their respective apertures and into their respective portions of bone while at least a portion of tension band plate 1000 is disposed against the portions of bone proximate to the unreduced fracture and as at least a portion of tension band plate 1000 conforms to the portions of bone proximate to the fracture.

Example Methods of Manufacture

Figure 9:
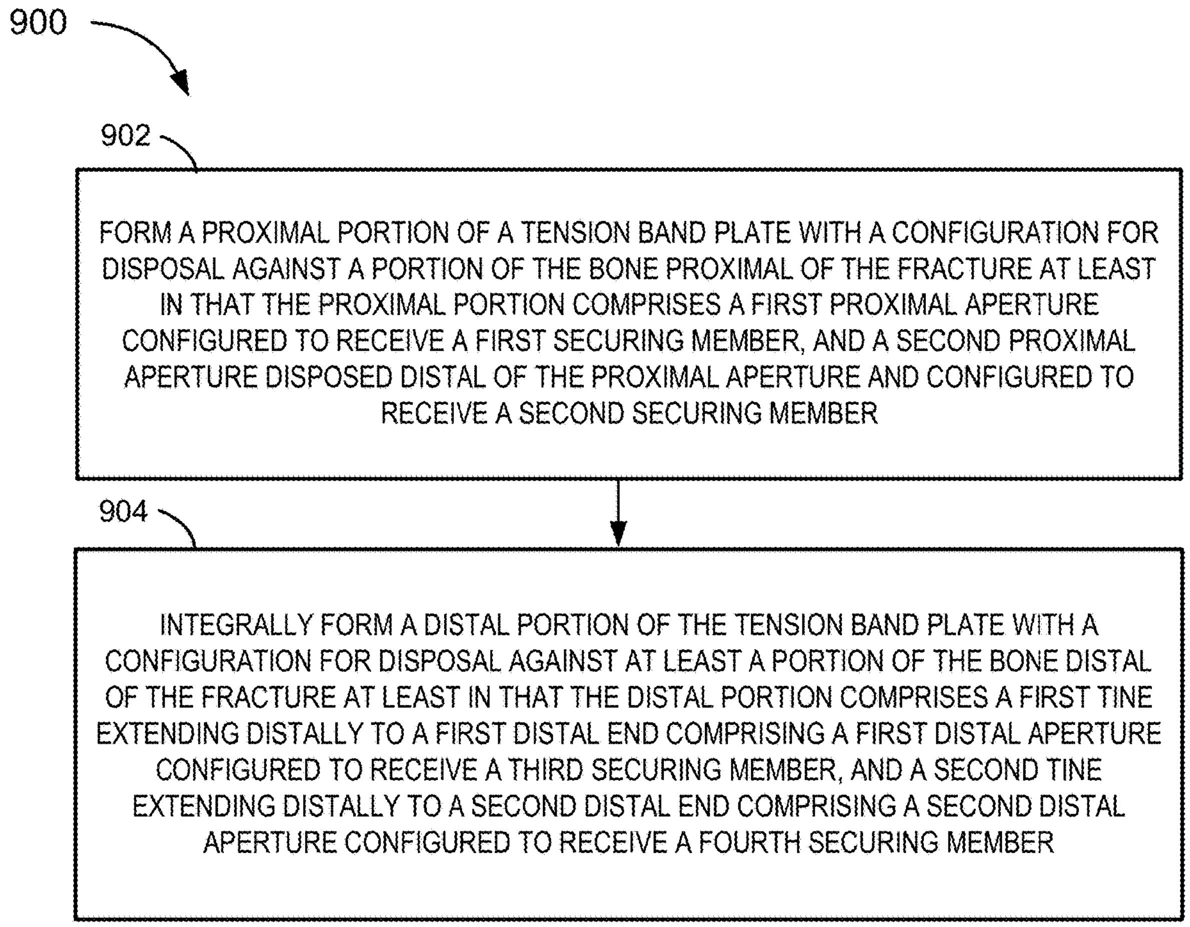
FIG. 9 illustrates a flowchart related to a method of manufacturing a tension band plate for treatment of bone fractures, in accordance with some example embodiments.

The disclosure now turns to FIG. 9 and one or more example methods of manufacturing a tension band plate for treatment of tibial fractures, as described anywhere in this disclosure. Although particular steps are described herein, the present application is not so limited and alternative methods may include a subset of these steps, in the same or different order, and may additionally include one or more additional steps not described herein.

Step 902 includes forming a proximal portion of a tension band plate with a configuration for disposal against a portion of the bone proximal of the fracture at least in that the proximal portion comprises a first proximal aperture configured to receive a first securing member, and a second proximal aperture disposed distal of the first proximal aperture and configured to receive a second securing member.

For example, as previously described in connection with at least FIGS. 2-7, proximal portion 210 of tension band plate 200 may be formed configurated for disposal against a portion of bone 100 proximal of fracture 110 at least in that proximal portion 210 comprises first proximal aperture 202 configured to receive first securing member 610, and second proximal aperture 204 disposed distal of first proximal aperture 202 and configured to receive a second securing member (not shown).

Where this method is utilizing to manufacture plate 1000, step 902 may alternatively comprise forming medial portion 1030 comprising aperture 1004 and integrally forming proximal portion 1010 with a configuration for disposal against a portion of the bone proximal of the fracture at least in that the proximal portion comprises a first proximal tine 1022*c* extending distally to a first proximal end 1024*c*, 1024*d* comprising first proximal aperture 1026*a* configured to receive a first securing member, and a second proximal tine 1022*c* extending proximally to second proximal end 1022*d* comprising second proximal aperture 1026*d* configured to receive a second securing member.

Step 904 includes integrally forming a distal portion of the tension band plate with a configuration for disposal against at least a portion of the bone distal of the fracture at least in that the distal portion comprises a first tine extending distally to a first distal end comprising a first distal aperture configured to receive a third securing member, and a second tine extending distally to a second distal end comprising a second distal aperture configured to receive a fourth securing member.

For example, as previously described in connection with at least FIGS. 2-7, distal portion 220 of tension band plate 200 may be formed configured for disposal against at least a portion of bone 105 distal of fracture 110 at least in that distal portion 220 comprises first tine 220*a* extending distally to first distal end 224*a* comprising first distal aperture 226*a* configured to receive third securing member 620*a*, and second tine 222*b* extending distally to second distal end 224*b* comprising second distal aperture 226*b* configured to receive fourth securing member 620*b*. At least first and second tines 222*a*, 222*b* are formed with a configuration for wrapping around and conforming to portions of bone 100, 105 proximate to fracture 110 and, thereby, a configuration for converting tensile forces at the fracture into compressive forces when first securing member 610 is secured through first proximal aperture 202 and into bone 100 proximal of fracture 110, and third and fourth securing members 620*a*, 620*b* are driven through respective first and second distal apertures 226*a*, 226*b*, into bone 105 distal of fracture 110, and perpendicular to and through the plane of fracture 110.

Where this method is utilized to manufacture plate 1000, step 904 may similarly comprise forming distal portion 1020 of tension band plate 1000 with a configuration for disposal against at least a portion of the bone distal of the fracture at least in that distal portion 1020 comprises first tine 1022*a* extending distally to first distal end 1024*a* comprising first distal aperture 1026*a* configured to receive a third securing member, and second tine 1022*b* extending distally to second distal end 1024*b* comprising second distal aperture 1026*b* configured to receive a fourth securing member. In some embodiments, a method related to flowchart 900 may include manufacturing tension band plate 200 such that a thickness of the tension band plate decreases from a first thickness $T_1$ at proximal portion 210 to a second thickness $T_2$ less than the first thickness along at least first and second tines 222*a*, 222*b* of distal portion 220, thereby allowing first and second tines 222*a*, 222*b* to be manually bent to match a contour of at least portion 105 of bone 100 distal of fracture 110.

Where this method is utilized to manufacture plate 100, a method related to flowchart may include manufacturing tension band plate 1000 such that a thickness of the tension band plate decreases from a first thickness $T_1$ at medial portion 1030 to a second thickness $T_2$ less than the first thickness along at least first and second tines 1022*a*, 1022*b*, 1022*c*, 1022*d* of distal and proximal portions 1020, 1010, thereby allowing tines 1022*a*, 1022*b*, 1022*c*, 1022*d* to be manually bent to match a contour of at least a portion of the bone distal of the fracture.

In some embodiments, a method related to flowchart 900 may include forming proximal and distal portions 210, 220 to have an edge profile with a substantially vertical side with height $H_1$ extending from a bottom edge and a rounded upper edge.

In some embodiments, a method related to flowchart 900 may include forming scalloped portion 240 (or portions 1040) that separates and defines a border between proximal portion 210 and distal portion 220 (or between medial portion 1030 and each of proximal and distal portions 1010, 1020).

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The invention claimed is:

1. An orthopedic tension band plate for treatment of a fracture in a bone, comprising:
- a proximal portion configured to be disposed against a portion of the bone proximal of the fracture, the proximal portion extending along a longitudinal centerline of the tension band plate and comprising:
  - a first proximal aperture configured to receive a first securing member, and
  - a second proximal aperture disposed distal of the first proximal aperture and configured to receive a second securing member;
- a distal portion extending along the longitudinal centerline and configured to be disposed against at least a portion of the bone distal of the fracture, the distal portion comprising:
  - a first tine extending distally to a first distal end comprising a first distal aperture configured to receive a third securing member, wherein a proximal portion of the first tine extends at a first angle laterally away from the longitudinal centerline and a distal portion of the first tine extends from the proximal portion at a second angle with respect to the longitudinal centerline that is smaller than the first angle, and
  - a second tine extending distally to a second distal end comprising a second distal aperture configured to receive a fourth securing member,
- wherein at least the first and second tines are configured to wrap around and conform to portions of the bone proximate to the fracture and, thereby, convert tensile forces at the fracture into compressive forces when:
  - the third and fourth securing members are secured through the respective first and second distal apertures, into the bone distal of the fracture,
  - the second securing member is secured through the second proximal aperture and into the bone proximal of the fracture, and
  - the first securing member is secured through the first proximal aperture and into the bone proximal of the fracture and proximal of the second securing member.

2. The orthopedic tension band plate of claim 1, wherein the second proximal aperture is disposed along a centerline of the tension band plate that extends longitudinally through the proximal and distal portions.

3. The orthopedic tension band plate of claim 1, wherein at least the first and second tines are unbent until at least the third and fourth bone screws are secured through the respective first and second distal apertures, into the bone distal of the fracture, and perpendicular to and through the plane of the fracture.

4. The orthopedic tension band plate of claim 1, wherein:
- the first angle is approximately 10 degrees from parallel with the longitudinal centerline; and
- the second angle is approximately 5 degrees from parallel with the longitudinal centerline,
- thereby allowing at least the first and second tines to wrap around and conform to the portion of the bone distal of the fracture.

5. The orthopedic tension band plate of claim 1, wherein relative spacings between any two of the first proximal aperture, the second proximal aperture, the first distal aperture and the second distal aperture are set to adequately capture the fracture of the bone.

6. The orthopedic tension band plate of claim 1, wherein a thickness of the tension band plate decreases from a first thickness at the proximal portion to a second thickness less than the first thickness along at least the first and second tines of the distal portion, thereby allowing the first and second tines to be manually bent to match a contour of at least the portion of the bone distal of the fracture.

7. The orthopedic tension band plate of claim 1, comprising an edge profile having a substantially vertical side extending from a bottom edge and a rounded upper edge.

8. The orthopedic tension band plate of claim 1, comprising a scalloped portion separating and defining a border between the proximal portion and the distal portion.

9. The orthopedic tension band plate of claim 8, wherein a width of the first portion tapers to a minimum width at the scalloped portion, thereby reducing resistance of the tension band plate to conform to a contour of the bone.

10. The orthopedic tension band plate of claim 1, wherein the tension band plate is configured to automatically reduce the fracture as the tension band plate conforms to the portions of the bone proximate to the fracture.

11. The orthopedic tension band plate of claim 1, wherein the first securing member, the second securing member, the third securing member and the fourth securing member each comprises one of a bone screw, a pin, a wire or a post.

12. The orthopedic tension band plate of claim 1, wherein the first proximal aperture, the second proximal aperture, the first distal aperture and the second distal aperture each comprises one of a standard locking hole, a compression/gliding hole, and a locking compression/gliding hole.

13. A method of utilizing an orthopedic tension band plate for treatment of a fracture in a bone, comprising:
- disposing at least a portion of the tension band plate proximate to the fracture and against the bone, the tension band plate comprising:
  - a proximal portion extending along a longitudinal centerline of the tension band plate and comprising:
    - a first proximal aperture configured to receive a first securing member, and a second proximal aperture disposed distal of the first proximal aperture and configured to receive a second securing member; and a distal portion extending along the longitudinal centerline and comprising:

a first tine extending distally to a first distal end comprising a first distal aperture configured to receive a third securing member, wherein a proximal portion of the first tine extends at a first angle laterally away from the longitudinal centerline and a distal portion of the first tine extends from the proximal portion at a second angle with respect to the longitudinal centerline that is smaller than the first angle, and a second tine extending distally to a second distal end comprising a second distal aperture configured to receive a fourth securing member, driving the third and fourth securing members through the respective first and second distal apertures, into the bone distal of the fracture, and perpendicular to and through a plane of the fracture; and driving the first securing member through the first proximal aperture and into the bone proximal of the fracture, thereby:

causing at least the first and second tines to wrap around and conform to portions of the bone proximate to the fracture, pulling the proximal portion into contact with a portion of the bone proximal of the fracture, and converting tensile forces at the fracture into compressive forces.

14. The method of claim 13, further comprising driving the second securing member through the second proximal aperture and into the bone proximate of the fracture, the second proximal aperture disposed along a centerline of the tension band plate that extends longitudinally through the proximal and distal portions.

15. The method of claim 13, wherein at least the first and second tines are unbent until at least the third and fourth securing members are driven through the respective first and second distal apertures, into the bone distal of the fracture, and perpendicular to and through the plane of the fracture.

16. The method of claim 13, wherein:

the first angle is approximately 10 degrees from parallel with the longitudinal centerline; and the second angle is approximately 5 degrees from parallel with the longitudinal centerline, thereby allowing at least the first and second tines to wrap around and conform to the portion of the bone distal of the fracture.

17. The method of claim 13, wherein relative spacings between any two of the first proximal aperture, the second proximal aperture, and the first and second distal apertures are set to adequately capture the fracture of the bone.

18. The method of claim 13, wherein a thickness of the tension band plate decreases from a first thickness at the proximal portion to a second thickness less than the first thickness along at least the first and second tines of the distal portion, thereby allowing the first and second tines to be manually bent to match a contour of at least the portion of the bone distal of the fracture.

19. The method of claim 13, wherein the tension band plate comprises an edge profile having a substantially vertical side extending from a bottom edge and a rounded upper edge.

20. The method of claim 13, wherein the tension band plate comprises a scalloped portion separating and defining a border between the proximal portion and the distal portion.

21. The method of claim 20, wherein a width of the first portion tapers to a minimum width at the scalloped portion, thereby reducing resistance of the tension band plate to conform to a contour of the bone.

22. The method of claim 13, comprising automatically reducing the fracture by driving the first, second, third and further securing members into the respective portions of the bone while at least a portion of the tension band plate is disposed against the portions of the bone proximate to the unreduced fracture and as at least a portion of the tension band plate conforms to the portions of the bone proximate to the fracture.

23. A method of manufacturing an orthopedic tension band plate for treatment of a fracture in a bone, comprising:

forming a proximal portion of the tension band plate extending along a longitudinal centerline of the tension band plate and with a configuration for disposal against a portion of the bone proximal of the fracture at least in that the proximal portion comprises:

a first proximal aperture configured to receive a first securing member, and a second proximal aperture disposed distal of the first proximal aperture and configured to receive a second securing member;

integrally forming a distal portion of the tension band plate extending along the longitudinal centerline and with a configuration for disposal against at least a portion of the bone distal of the fracture at least in that the distal portion comprises:

a first tine extending distally to a first distal end comprising a first distal aperture configured to receive a third securing member, wherein a proximal portion of the first tine extends at a first angle laterally away from the longitudinal centerline and a distal portion of the first tine extends from the proximal portion at a second angle with respect to the longitudinal centerline that is smaller than the first angle, and a second tine extending distally to a second distal end comprising a second distal aperture configured to receive a fourth securing member, wherein at least the first and second tines are formed with a configuration for wrapping around and conforming to portions of the bone proximate to the fracture and, thereby, a configuration for converting tensile forces at the fracture into compressive forces when:

the third and fourth securing members are secured through the respective first and second distal apertures, into the bone distal of the fracture, the second securing member is secured through the second proximal aperture and into the bone proximal of the fracture, and the first securing member is secured through the first proximal aperture and into the bone proximal of the fracture and proximal of the second securing member.

24. The method of claim 23, wherein the second proximal aperture is disposed along a centerline of the tension band plate that extends longitudinally through the proximal and distal portions.

25. The method of claim 23, wherein at least the first and second tines are unbent until at least the third and fourth securing members are driven through the respective first and second distal apertures, into the bone distal of the fracture, and perpendicular to and through the plane of the fracture.

26. The method of claim 23, wherein:

the first angle is approximately 10 degrees from parallel with the longitudinal centerline; and the second angle is approximately 5 degrees from parallel with the longitudinal centerline, thereby allowing at least the first and second tines to wrap around and conform to the portion of the bone distal of the fracture.

27. The method of claim 23, wherein relative spacings between any two of the first proximal aperture, the second proximal aperture, and the first and second distal apertures are set to adequately capture the fracture of the bone.

28. The method of claim 23, further comprising manufacturing the tension band plate such that a thickness of the tension band plate decreases from a first thickness at the proximal portion to a second thickness less than the first thickness along at least the first and second tines of the distal portion, thereby allowing the first and second tines to be manually bent to match a contour of at least the portion of the bone distal of the fracture.

29. The method of claim 23, comprising forming the proximal and distal portions to have an edge profile with a substantially vertical side extending from a bottom edge and a rounded upper edge.

30. The method of claim 23, comprising forming a scalloped portion that separates and defines a border between the proximal portion and the distal portion.

31. The method of claim 30, wherein the first portion is formed to have a width that tapers to a minimum width at the scalloped portion, thereby reducing resistance of the tension band plate to conform to a contour of the bone.

32. The method of claim 23, wherein the tension band plate is configured to automatically reduce the fracture as the tension band plate conforms to the portions of the bone proximate to the fracture.

* * * * *